United States Patent [19]

Knudson

[11] Patent Number: 5,115,133
[45] Date of Patent: May 19, 1992

[54] TESTING OF BODY FLUID CONSTITUENTS THROUGH MEASURING LIGHT REFLECTED FROM TYMPANIC MEMBRANE

[75] Inventor: Mark B. Knudson, Arden Hills, Minn.
[73] Assignee: Inomet, Inc., Minneapolis, Minn.
[21] Appl. No.: 510,935
[22] Filed: Apr. 19, 1990
[51] Int. Cl.⁵ .......................................... G01N 33/48
[52] U.S. Cl. .................................... 250/341; 356/41; 128/633; 128/664
[58] Field of Search .................. 356/41; 250/341, 343; 128/633, 664

[56] References Cited

U.S. PATENT DOCUMENTS

| | | | |
|---|---|---|---|
| 2,414,747 | 1/1947 | Kirschbaum | 356/41 |
| 3,054,397 | 9/1982 | Benzinger | 128/2 |
| 3,054,893 | 9/1962 | Dasburg | 246/182 |
| 3,156,117 | 11/1964 | Benzinger | 73/359 |
| 3,282,106 | 11/1966 | Barnes | 73/355 |
| 3,463,142 | 8/1969 | Harte | 128/2 |
| 3,825,342 | 7/1974 | Lubbers et al. | 356/41 |
| 3,878,836 | 4/1975 | Twentier | 128/9 |
| 3,949,740 | 4/1976 | Twentier | 128/9 |
| 3,958,560 | 5/1976 | March | 128/2 |
| 4,014,321 | 3/1977 | March | 128/2 |
| 4,086,915 | 5/1978 | Kofsky et al. | 128/2 |
| 4,169,676 | 10/1979 | Kaiser | 356/39 |
| 4,195,641 | 4/1980 | Johnes et al. | 128/632 |
| 4,223,680 | 9/1980 | Jobsis | 128/633 |
| 4,281,646 | 8/1981 | Kinoshita | 128/6 |
| 4,344,438 | 8/1982 | Schultz | 128/634 |
| 4,407,290 | 10/1983 | Wilbur | 128/633 |
| 4,427,889 | 1/1984 | Muller | 250/339 |
| 4,575,237 | 3/1986 | Suzuki | 356/1 |
| 4,602,642 | 7/1986 | O'Hara et al. | 128/664 |
| 4,622,974 | 11/1986 | Coleman et al. | 128/634 |
| 4,655,225 | 4/1987 | Dahne et al. | 128/633 |
| 4,662,360 | 5/1987 | O'Hara et al. | 128/9 |
| 4,685,463 | 8/1987 | Williams | 128/632 |
| 4,704,029 | 11/1987 | Van Heuvelen | 356/39 |
| 4,750,830 | 6/1988 | Lee | 351/211 |
| 4,772,561 | 9/1988 | Genshaw | 436/169 |
| 4,790,324 | 12/1988 | O'Hara et al. | 128/664 |
| 4,800,886 | 1/1989 | Nestor | 128/634 |
| 4,805,623 | 2/1989 | Jobsis | 128/633 |
| 4,850,365 | 7/1989 | Rosenthal | 128/664 |
| 4,854,699 | 8/1989 | Edgar, Jr. | 356/41 |
| 4,882,492 | 11/1989 | Schlager | 250/346 |
| 4,926,867 | 5/1990 | Kanda et al. | 128/633 |

FOREIGN PATENT DOCUMENTS

| | | |
|---|---|---|
| 0160768 | 5/1984 | European Pat. Off. |
| 381608 | 8/1990 | European Pat. Off. |
| 3619442 | 12/1987 | Fed. Rep. of Germany |
| 3910749 | 10/1990 | Fed. Rep. of Germany |
| 1526973 | 1/1987 | France |
| WO89/11825 | 12/1989 | PCT Int'l Appl. |
| 2033575A | 8/1979 | United Kingdom |
| 2055476 | 3/1981 | United Kingdom |

OTHER PUBLICATIONS

"Blood Glucose Measurement by Multiple Attenuated Total Reflection", IEEE Trans. on Biomedical Eng., vol. 37, No. 5, May 1990.

An article entitled, "Determination of Physiological Levels of Glucose in an Aqueous Matrix with Digitally Filtered Fourier Transform Near-Infrared Spectra", by Arnold et al., published in *Analytical Chemistry*, vol. 92, No. 14, Jul. 15, 1990.

Primary Examiner—Carolyn E. Fields
Assistant Examiner—James E. Beyer
Attorney, Agent, or Firm—Merchant, Gould, Smith, Edell, Welter & Schmidt

[57] ABSTRACT

An apparatus and method are disclosed for determining a level of a constituent such as glucose in a body fluid such as blood. The apparatus and method utilize a light generator for generating a testing light of known intensity with the testing light including a wavelength absorbable by the constituent being measured. The light generator also generates a reference light of known intensity having a wavelength not absorbable by the constituent being measured. The testing light and reference light are directed toward a fluid containing an unknown concentration of a constituent. A light detector is provided for measuring the intensity of the testing light and reference light being spectrally modified by the fluid. A light path distance measurer is provided for measuring a distance of a light path traveled by the testing light and reference light. A circuit is provided for calculating a level of the constituent in the fluid in response to a reduction in intensity of the testing light and reference light and in response to the measured distance.

69 Claims, 2 Drawing Sheets ics and method for testing blood constituents. More particularly, this application pertains to such apparatus and methods utilizing spectrophotometric analysis of blood constituents.

TESTING OF BODY FLUID CONSTITUENTS THROUGH MEASURING LIGHT REFLECTED FROM TYMPANIC MEMBRANE

BACKGROUND OF THE INVENTION

1. Field of the Invention

This patent application pertains to an apparatus and method for testing blood constituents. More particularly, this application pertains to such apparatus and methods utilizing spectrophotometric analysis of blood constituents.

2. Description of the Prior Art

The use of spectrophotometric methods to quantitatively determine the concentration of a blood constituent are known. For example, U.S. Pat. No. 4,882,492 to Schlager teaches a non-invasive near-infrared measurement of blood analyte concentrations. The Schlager patent is particularly directed to the measurement of blood glucose levels. The Schlager patent recognizes that certain wavelengths of light in the near-infrared spectrum are absorbed by glucose. Modulated light is directed against a tissue (shown as an earlobe). The light is either passed through the tissue or impinged on a skin surface. The light is spectrally modified in response to the amount of analyte (for example, glucose) in the blood and tissue. The spectrally modified light is split with one beam passed through a correlation cell. The other beam is passed through a reference cell. The intensity of the beams passing through the correlation cell and the reference cell are compared to calculate a glucose concentration in the sample.

U.S. Pat. No. 4,805,623 to Jobsis teaches a spectral photometric method for quantitatively determining the concentration of a component in human blood. The Jobsis method teaches various steps including the determination of an apparent effective path length for the light which is being absorbed by the constituent being measured.

U.S. Pat. No. 4,655,225 to Dahne et al. teaches a spectrophotometric method and apparatus for non-invasive testing. The Dahne patent is particularly directed to the measurement of blood glucose.

U.S. Pat. Nos. 4,014,321 and 3,958,560 to March teach non-invasive glucose sensor systems which involve passing light through the cornea of the patient.

Notwithstanding the developments in the art, a need for an improved spectrophotometric measurement apparatus and method persists. For example, systems and methods which require the calculation of an apparent light pathway are susceptible to inaccuracy. Such a system is shown in the aforementioned U.S. Pat. No. 4,805,623. Systems which have fixed dimensioned light pathways (for example, U.S. Pat. 4,014,321) are restricted in their use and practicality. It is also desirable to develop a system and apparatus which can be used for non-invasive testing as well as invasive testing (for example, as a continuous monitor for testing blood glucose level during surgery or insulin treatment). Further, it is desirable to develop a system which can be used in conjunction with a chemical emission system (such as a blood glucose monitoring system which controls an insulin administering apparatus).

SUMMARY OF THE INVENTION

According to a preferred embodiment of the present invention, an apparatus and method are disclosed for determining a level of a constituent such as glucose in a body fluid such as blood. The apparatus and method comprises a light generator for generating a testing light of known intensity with the testing light including a wavelength absorbable by the constituent being measured. The testing light is directed toward the fluid. A light detector is provided for measuring an intensity of the testing light reflected from the fluid. A light path distance measurer is provided for measuring a distance of a light path from the light generator to the light detector via the fluid. A circuit is provided for calculating a level of the constituent in the fluid in response to a reduction in intensity of the testing light between the light generator and the light detector and in response to the measured distance.

DESCRIPTION OF A PREFERRED EMBODIMENT

Figure 1:
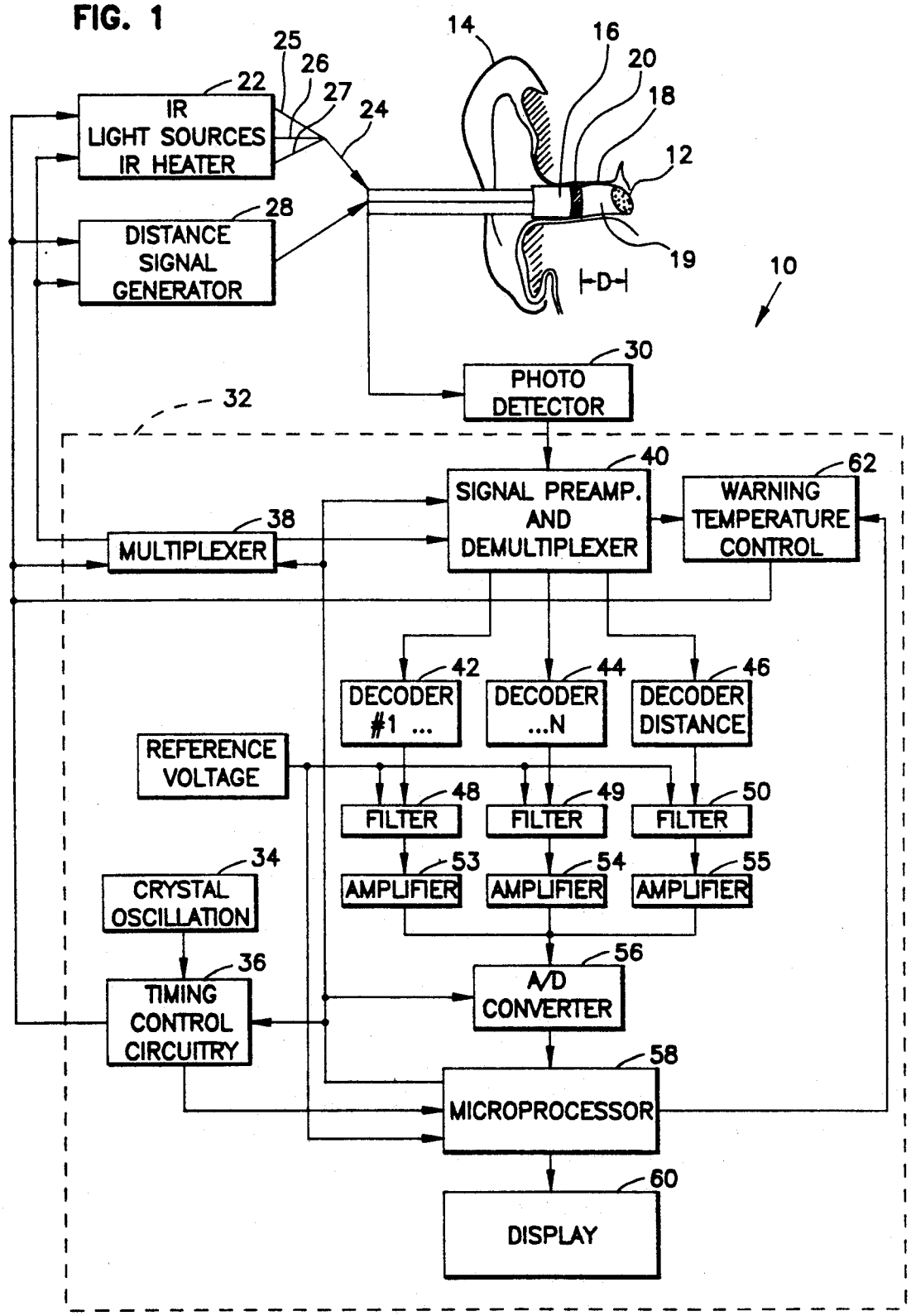
FIG. 1 is a schematic representation of the apparatus of the present invention showing its use in an embodiment for measuring a constituent within blood vessels in a tympanic membrane.

Referring now to FIG. 1, a detailed description of the preferred embodiment of the present invention will now be provided. In the embodiment shown, the present invention is shown for use in non-invasive testing for a particular blood constituent—namely, blood glucose. Also, in the embodiment of FIG. 1, the present invention is shown in use for measuring blood glucose in blood vessels in a tympanic membrane. While the illustrated application is a preferred embodiment, it will be appreciated that the salient features of the present invention are applicable to a wide variety of body constituents. For example, glucose as well as other body constituents could be measured in a plurality of body fluids such as blood, crevicular fluid, and peritoneal fluid. The salient features of the invention, as will be more fully described include the measurement of an actual light path of a testing light containing a wavelength absorbable by the constituent to be measured and calculating a constituent level in response to the amount of absorption of the wavelength and in response to the measured light path distance. These and further salient features of the present invention shall now be more fully described.

In FIG. 1, the apparatus 10 is shown in use for measuring blood glucose within blood vessels of a tympanic membrane 12 in a human ear 14. (The apparatus 10 is also suitable for veterinary uses.) In the embodiment now being described, the apparatus 10 is non-invasive (i.e., no penetration of body tissue is required).

The apparatus 10 includes a distal end which carries a speculum 16. Speculum 16 is preferably disposable and is sized to be received within the auditory canal 18 of an ear 14. The speculum is selected to block the auditory canal 18 to prevent ambient light from entering the ear past the speculum 16. Accordingly, the speculum 16 closes the auditory canal 18 to define a closed testing volume 19 between the speculum 16 and the tympanic membrane 12. The actual distance D between the source of light in the speculum 16 and the tympanic membrane 12 will vary with each use of the apparatus 10. However, as will be more fully described, the present invention includes means for measuring the distance D.

For reasons that will become apparent, the speculum 16 has a tip 20 which opposed the tympanic membrane 12 upon insertion of the speculum into the auditory canal 18. The tip 20 is selected to pass certain predetermined light wavelengths (e.g. wavelengths which are absorbable by constituents which are to be measured).

In a preferred example of measuring glucose within the tympanic membrane 12, the tip 20 is selected to pass infrared and near-infrared light wavelengths. It will be appreciated that a speculum such as speculum 16 having an infrared and near-infrared transparent tip 20 is known in the art. An example of such is shown in U.S. Pat. No. 4,662,360. Such prior art speculums have been developed for use with tympanic thermometers. The speculums of such thermometers would be inserted within the auditory canal and would permit infrared radiation generated by a tympanic membrane to pas through the tip of the speculum toward infrared radiation detecting apparatus contained within the speculum. With such prior art apparatus, a healthcare provider can measure body temperature by detecting infrared radiation emitted from the tympanic membrane. Examples of complete apparatus for measuring body temperature from the tympanic membrane are shown in U.S. Pat. Nos. 4,602,642; 3,949,740; 3,878,836 and 4,790,324.

The present invention contemplates the generation of a testing light (including visible or non-visible wavelengths) which includes a wavelength absorbable by the constituent to be measured (for example, blood glucose). Shown schematically in FIG. 1, the present invention includes a generator 22 of near-infrared and infrared light sources. Generator 22 may be a lasing diode or a broad band light source with a filter.

The generator 22 is selected to generate a testing light of known intensity which includes a wavelength absorbable by the constituent to be tested. The generator 22 also includes means for generating one or more reference lights of known intensity having a wavelength which is not absorbable by the constituent to be measured. Also, for reasons that will be described, the generator 22 includes means for generating infrared radiation of a heating wavelength selected to be directed for the purpose of warming the tympanic membrane 12 and volume 19.

A fiber optic cable 24 is passed from the generator 22 into the speculum 16 to be directed toward and oppose the tympanic membrane 12 upon insertion of the speculum 16 into the auditory canal 18. An alternative to using cable 24 would be for the generator 22 to be a light diode within the speculum 16.

The reader will note that the wavelengths of the testing light, the reference light and the infrared heating radiation will all be passed by tip 20 toward tympanic membrane 12. In the preferred embodiment, the testing light will include a glucose sensitive wavelength of about 500 to about 4000 wave numbers ($cm^{-1}$). The non-absorbable reference light will have a preferred wavelength of about the same wavelength (e.g. an absorbable wavelength of 1040 wave numbers and a non-absorbable wavelength of 1150 wave numbers).

If it is desirable to test for constituents in addition to glucose, the generator 22 is simply selected to generate additional wavelengths selected for their absorbability by the desired constituent. In the schematic representation of FIG. 1, three optical paths 25-27 are shown for directing the infrared and near-infrared radiation toward the tympanic membrane 12. In a preferred embodiment, all light signals will be passed through a single optical fiber 24 with the light signals being multiplexed as will be described.

Including being coupled to light generator 22, the speculum 16 is coupled with a distance signal generator 28. Distance signal generator 28 includes means for generating a signal for use in measuring the distance D from the speculum 16 to the tympanic member 12. In a preferred embodiment, the distance signal generator 28 is an ultrasonic generator which will measure the distance D through Doppler measurements. However, the present invention need not be limited to such an embodiment. For example, light distance measuring techniques can also be employed. In such a case, the functions of generators 22 and 28 can be merged with the light passing through fiber cable 24 also being utilized to measure the distance D.

Finally, the distal end of the apparatus 10 is connected to a photo diode and distance signal detector 30 which detects and measures the desired wavelengths and signals reflected back from the tympanic membrane 12. Preferably, detector 30 will include means for detecting the temperature of volume 19. As previously described, tympanic temperature measurement is well known.

A circuit 32 (shown schematically in FIG. 1) is provided for calculating the level of the constituent in the blood in response to a reduction in intensity of the testing light between the light generator 22 and the detector 30. The circuitry, through algorithms which will be described, compares the reduction in intensity with a reduction in intensity of the non-absorbable wavelength and with the measured distance D. In response to the measured variables, the circuit 32 calculates the glucose level in the blood in the tympanic membrane 12.

The circuit 32 includes a crystal oscillator 34 for driving the circuitry 32. Timing control circuitry 36 is provided for synchronizing the light generation and detection of the apparatus 10. A multiplexer 38 is provided for multiplexing the signals and light pulses to be generated by generators 22 and 28.

A signal preamplifier and demultiplexer 40 is provided for receiving the detected signals from detector 30 and amplifying and demultiplexing into individual signals representing the intensity of the reflected absorbable and non-absorbable wavelengths, the temperature of volume 19 and a signal to be used in calculating distance D. In the preferred embodiment, at least two light wavelengths (a wavelength absorbable by glucose and a reference wavelength not absorbable by glucose) are anticipated. However, in FIG. 1, up to N wavelengths are disclosed representing the utility of the present invention for testing for multiple blood constituents and having multiple reference wavelengths. The first wavelength signal (for example, the testing light wavelength absorbable by glucose) is admitted to a first decoder 42. Other signal wavelengths (such as the reference wavelength not absorbable by glucose) is admitted to additional decoders such as decoder 44 (labeled decoder N in FIG. 1). A decoder 46 is also provided for decoding a signal representing the detection of the signal from the distance signal generator 28. The decoders place the demultiplexed signals in proper sequence.

All decoded signals are passed through filters 48–50 (for noise filtration) and subsequently through amplifiers 53-55. The amplified signals are passed through an analog-digital converter 56 to a microprocessor 58. Within the microprocessor 58, the signals are analyzed for the purposes of calculating the distance D and comparing the reduction in intensities between the absorbable wavelength and the non-absorbable wavelength for the purposes of determining the concentration of glucose within the blood in the tympanic membrane. A display 60 is provided for displaying to a healthcare provider the measured unknown (i.e., the blood glucose concentration).

It will be appreciated that circuitry for generating multiplexed infrared light and near-infrared light is well known and forms no part of this invention per se. It will also be appreciated that circuitry and apparatus for measuring distances (such as distance D) through either ultrasonic or light measurements (including Doppler measurements) are well known. Also, it will be appreciated that apparatus and circuitry for detecting reflected light and demultiplexing signals are well known. Further, it will be appreciated that algorithms for calculating blood constituent levels in response to measured reductions in near-infrared light intensities are well known.

The foregoing description identifies structure and apparatus and a method of testing which eliminates certain of the disadvantages of the prior art. For example, multiple constituents may be tested through non-invasive testing by multiplexing a plurality of wavelengths which are selectively absorbable by the blood constituents to be measured. The present invention also utilizes a warming circuit 62 for controlling the intensity of an infrared heater wavelength generated by generator 22. The warming circuitry 62 receives a signal from preamplifier 40 representing the temperature of volume 19 and tympanic membrane 12. In response to the signal, circuitry 62 controls generator 22 to heat and control the temperature of the tympanic membrane 12 and the auditory canal 18 to a sufficient elevated temperature to ensure that blood vessels within the tympanic membrane 12 remain open and that the measured absorption wavelengths do not shift due to temperature change. As a result, the present apparatus and method have enhanced reliability over the prior art.

Importantly, the present invention measures the exact distance D that light is traveling from its source to the sample and back to a detection apparatus. It will be recognized that in spectrophotometric methods, the measurement of a distance of the light path is essential since the reduction in intensity of the absorbable wavelength is a function of the distance it is traveling as well as the concentration of the constituent to be measured. Prior art apparatus for measuring blood glucose and other body constituents were not capable of measuring the actual light path distance which could vary from test to test. Instead, prior art apparatus had a fixed light path distance (see, for example, U.S. Pat. No. 4,014,321) or required the measurement of a so called "apparent" light path distance see, for example, U.S. Pat. No. 4,805,623).

The foregoing description disclosed two principle aspects of the present invention: (1) a comparison of reduction in intensity between an absorbable and a non-absorbable wavelength and (2) the calculation of the precise light path distance traveled by the absorbable and non-absorbable wavelengths. The utilization of these elements in combination with temperature control of the test area result in a blood constituent measurement device which is particularly suitable for non-invasive testing.

In the preferred example, the apparatus is carried on the distal end of a device to be inserted within the auditory canal of an ear. This will provide a simple, quick and accurate testing of blood glucose in a patient. However, certain of the salient features of the present invention (such as, the measurement of the precise distance and comparing reduction in intensity between non-absorbable and absorbable wavelengths) is also suitable for use in in vivo testing.

Figure 2:
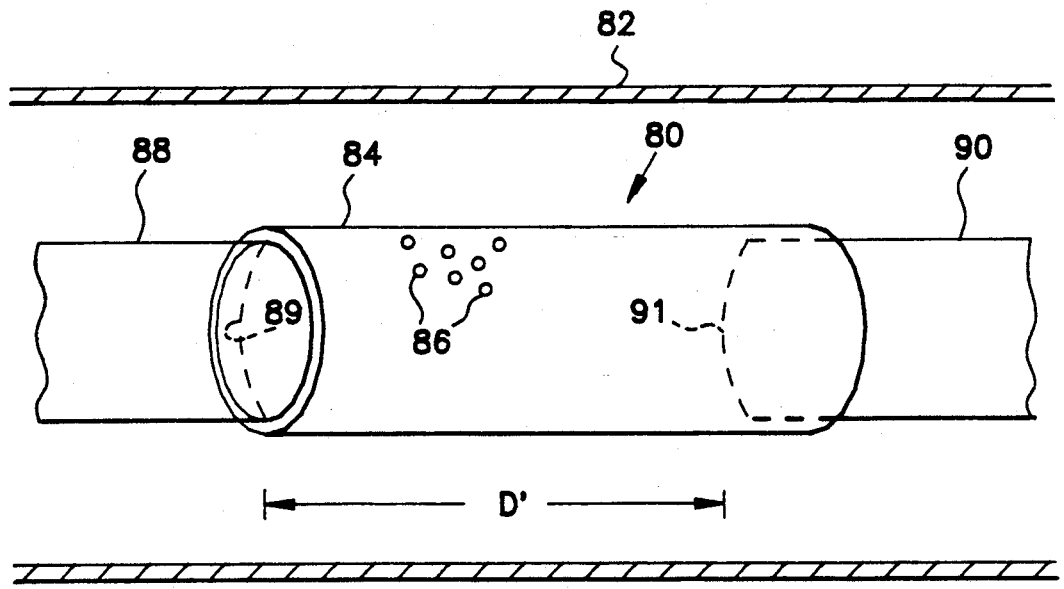
FIG. 2 is a view of an apparatus according to the present invention for use in invasive testing for blood glucose.

A particular structure for an in vivo application is shown in FIG. 2. In FIG. 2, a preferred apparatus 80 is shown inserted within a blood vessel 82. The apparatus 80, while shown in blood vessel 82, can be placed in any body cavity (e.g., the peritoneal cavity).

The apparatus 80 includes a generally cylindrical membrane 84. Preferably, membrane 84 is selected to be permeable to the blood constituent to be measured. In the case of measuring blood glucose, membrane 84 is preferably dialysis tubing having a molecular weight cutoff slightly greater than the molecular weight of glucose (i.e. greater than 180.16). To illustrate the permeability of membrane 84, holes 86 (shown greatly exaggerated in size) are provided passing through the membrane 84.

First and second optical fibers 88 and 90 are provided inserted into opposite ends of membrane 84. The fibers can be press, fit and sealed in membrane 84. First optical fiber 88 has a concave end 89 opposing a convex end 91 of second fiber 90. Concave end 89 directs light toward end 91.

As in the previously described embodiment, multiplexed light wavelengths can be passed through fiber 88 toward fiber 90. The multiplexed wavelengths will include a wavelength absorbable by glucose and a non-absorbable wavelength. The absorbable and non-absorbable wavelengths pass through the membrane 84 between fibers 88 and 90 and are passed from fiber 90 to the circuitry (not shown) such as that shown and described in the aforementioned embodiment. When passing through the membrane 84, the intensities of both the absorbable and non-absorbable wavelengths will be reduced. The absorbable wavelength will be particularly reduced in response to the concentration of glucose within the membrane 84. By comparing the reduction in intensities between the absorbable and non-absorbable wavelength, the concentration of glucose within the membrane (and hence in the blood) can be determined if the distance D' between ends 89, 91 is known.

To measure distance D', an additional wavelength can be multiplexed with the absorbable and non-absorbable wavelength. The additional wavelength is selected to be passed from fiber 88 toward fiber 90 and reflected back from fiber 90 as back reflection into fiber 88. Through Doppler measurement techniques, the reflected light can be utilized to measure the accurate distance D' between fibers 88 and 90. It will be appreciated that the phenomena of back reflection forms no part of this invention per se and can be accomplished through selecting particular wavelengths to reflect off of fiber 90 or through the additional use of partially reflective coatings on surface 91. As a result of Doppler measuring the distance D' between fibers 88 and 90, the present invention can compensate for distance variations between fibers 88 and 90 which may result from compression due to posture of the patient, thermal expansion, manufacturing tolerances and other causes.

Figure 3:
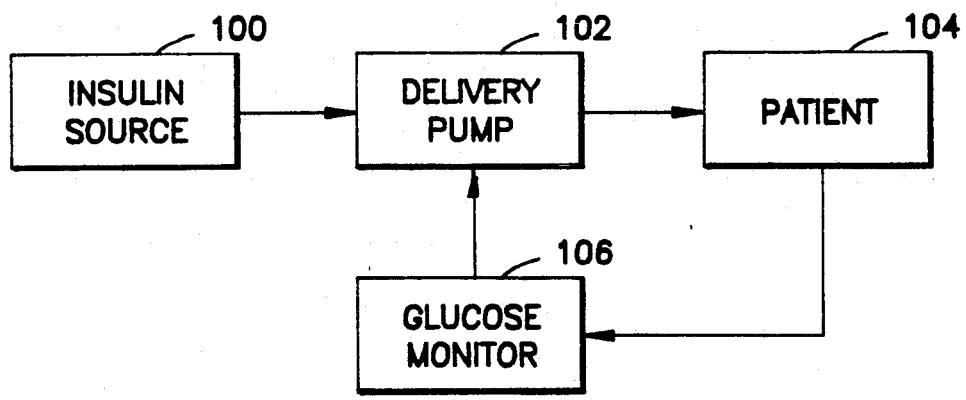
FIG. 3 is a schematic view of a system using the apparatus of the present invention to control admission of a drug to a patient.

The use of the in vivo apparatus 80 is particularly suitable for constantly monitoring the blood constituent level of a patient. Continuous monitoring is desireable during surgical procedures. Also, continuous monitoring permits feedback control of chemical admission to patients. For example, with reference to FIG. 3, it is schematically shown how the present invention can be utilized to control the admission of insulin to a patient. In FIG. 3, an insulin source 100 is shown connected via a delivery pump 102 to a patient 104. The apparatus of the present invention 106 (which includes the apparatus 80 plus the circuitry of FIG. 1 or just the entire apparatus 10 of FIG. 1) is shown connected to the patient 104 to constantly monitor the blood glucose of the patient. The measured blood glucose level of the patient as monitored by the present invention 106 is utilized to control the action of the delivery pump 102 in order to maintain the patient's blood glucose within predetermined tolerances of a desired blood glucose level.

Through the foregoing detailed description of the present invention, it has been shown how the objects of the present invention have attained in a preferred manner. However, modifications and equivalents of the disclosed concepts, such as those which would readily occur to one skilled in the art, are intended to be included within the scope of the claims of the present invention.

What is claimed is:

1. An apparatus for determining a level of a constituent in a body fluid, said apparatus comprising
   light generating means for generating a testing light of known intensity with said testing light including at least one wavelength absorbable by said constituent and directing said testing light toward said fluid;
   light detecting means for measuring an intensity of said testing light reflected from said fluid;
   light path measurement means for measuring an actual distance of a light path from said light generating means to said light detecting means via said fluid;
   circuit means for calculating a level of said constituent in said fluid in response to a reduction in intensity of said testing light between said light generating means and said light detecting means and in response to said actual distance measured by said light path measurement means.

2. An apparatus according to claim 1 wherein said light generating means includes means for generating at least two wavelengths including said testing light and a reference light of known intensity having at least one wavelength not absorbable by said constituent, said light detecting means including means for measuring said testing light and said reference light reflected from said fluid and said circuit means including means for comparing said measured intensities and using said measured intensity of said reference light as a reference for determining the amount of said testing light absorbed by said constituent.

3. An apparatus according to claim 2 comprising means for multiplexing said testing and reference lights emitted from said light generating means.

4. An apparatus according to claim 1 comprising heating means for controlling a temperature of said fluid.

5. An apparatus according to claim 1 wherein said light generating means, said light detecting means and said light path measurement means are disposed at a distal end of a housing.

6. An apparatus according to claim 5 wherein said body fluid is contained within a tympanic membrane and wherein said housing is sized to be received within an auditory canal of an ear with said distal end opposing said tympanic membrane.

7. An apparatus according to claim 6 wherein said distal end includes a material selected to pass said absorbable wavelength.

8. An apparatus according to claim 7 wherein said absorbable wavelength is infrared.

9. An apparatus according to claim 1 wherein said testing light includes a plurality of wavelengths absorbable by a plurality of different constituents and wherein said circuit means includes means for separately calculating the level of each of said constituents in response to a measured intensity of each of said wavelengths reflected from said fluid.

10. An apparatus according to claim 6 wherein said housing includes means for blocking ambient light from entering said auditory canal and reaching said distal end.

11. An apparatus according to claim 1 wherein said fluid is blood.

12. An apparatus according to claim 11 wherein said constituent is glucose.

13. An apparatus according to claim 1 wherein said fluid is crevicular fluid.

14. An apparatus according to claim 13 wherein said constituent is glucose.

15. An apparatus according to claim 1 wherein said fluid is peritoneal fluid.

16. An apparatus according to claim 15 wherein said constituent is glucose.

17. An apparatus according to claim 1 comprising admitting means for admitting a chemical to a body with a level of said constituent in said body fluid changing in response to an amount of said chemical admitted to said body, control means connecting said circuit means to said admitting means for varying an amount of said chemical admitted to said body in response to a level of said constituent calculated by said circuit means.

18. An apparatus according to claim 6 comprising heating means for heating said tympanic membrane to a temperature sufficient for fluid containing vessels in said tympanic membrane to be open.

19. An apparatus according to claim 6 comprising temperature detection means for detecting a temperature of said tympanic membrane.

20. An apparatus according to claim 19 comprising signal means indicating a measured temperature of said tympanic membrane has exceeded a maximum predetermined temperature range.

21. An apparatus according to claim 1 wherein said at least one wavelength is in a range of about 500 to about 4000 wave numbers.

22. An apparatus according to claim 21 wherein said at least one wavelength is about 1040 wave numbers.

23. An apparatus of determining a level of a blood constituent through non-invasive testing, said apparatus comprising:
   light generating means for generating testing light of known intensity and including a wavelength absorbable by said constituent;

light detecting means for measuring an intensity of light;

housing means having a distal end for carrying said light generating means and said light detecting means with said distal end sized to be received within an auditory canal of an ear with said light generating means and said light detecting means opposing a tympanic membrane;

light path measurement means for measuring an actual distance of a light path from said light generating means to said light detecting means via said tympanic membrane;

circuit means for calculating a level of said constituent in blood within blood vessels of said tympanic membrane in response to a reduction of intensity of said testing light between said light generating means and said light detecting means and in response to said measured actual distance.

24. An apparatus according to claim 23 wherein said light generating means includes means for generating at least two wavelengths including said testing light and the reference light having a wavelength not absorbable by said constituent, said light detecting means including means for measuring said testing light and said reference light reflected from said tympanic membrane, and in said circuit means including means for comparing said measured intensities and using said measured intensity of said reference light as a reference for determining the amount of said testing light absorbed by said constituent.

25. An apparatus according to claim 24 comprising means for multiplexing said testing and reference lights emitted from said light generating means.

26. An apparatus according to claim 23 comprising heating means for heating said tympanic membrane to a temperature sufficient for said blood vessels to be unrestricted.

27. An apparatus according to claim 23 wherein said distal end includes a material selected to pass said absorbable wavelength.

28. An apparatus according to claim 27 wherein said absorbable wavelength is infrared.

29. An apparatus according to claim 23 wherein said testing light includes a plurality of wavelengths absorbable by a plurality of different constituents wherein said circuit means includes means for separately calculating a level of each of said constituents in response to a measured intensity of each of said wavelengths reflected from said tissue 30. An apparatus according to claim 23 wherein said housing includes means for blocking ambient light from entering said auditory canal and reaching said distal end.

31. An apparatus according to claim 23 wherein said constituent is blood glucose.

32. An apparatus according to claim 23 wherein said wavelength is in a range of about 500 to about 4000 wave numbers.

33. An apparatus, according to claim 32 wherein said wavelength is about 1040 wave numbers.

34. A method of non-invasive testing of a blood constituent utilizing light generating means for generating a testing light of known intensity and including a wavelength absorbable by said constituent, light detecting means for measuring an amount of light reflected from a tissue containing blood, light path measurement means for measuring a distance of a light path from said light generating means to said light detecting means via said tissue and circuit means for calculating a level of said constituent in said tissue in response to a reduction in intensity of said testing light said light generating means and said light detecting means and in response to said measured distance, said method including the steps of:

locating said light generating means in a location for light from said light generating means to be directed to a tympanic membrane and reflected back toward said light detecting means;

directing said testing light to said tympanic membrane;

measuring an intensity of said testing light reflected by said tympanic membrane;

measuring an actual distance of said light path from said light generating means to said light detecting means via said tympanic membrane; and calculating a level of said constituent by comparing said measured and known intensities and allowing for an effect of said measured actual distance.

35. A method according to claim 34 wherein said method utilizes heating means for heating said tympanic membrane and said method includes the steps of heating said tympanic membrane to a temperature sufficient for blood vessels in said tympanic membrane to be unrestricted.

36. A method according to claim 34 wherein said light generating means includes means for generating at least two wavelengths including said testing light and a reference light of known intensity having a wavelength non-absorbable by said constituent, said light detecting means including means for measuring said testing light and said reference light reflected from said tympanic membrane and said circuit means including means for comparing said measured intensities and using said measured intensity of said reference light as a reference for determining the amount of said testing light absorbed by said constituent, said method including the step of directing said reference light towards the tympanic membrane and measuring an intensity of said reference light reflected off said tympanic membrane and calculating a level of said constituent by comparing a measured intensity of said reference light to a measured intensity of said testing light.

37. A method according to claim 36 comprising multiplexing said reference light and said testing light at said light generating means.

38. A method according to claim 34 wherein said constituent is glucose.

39. A method according to claim 34 wherein said wavelength of said testing light is infrared.

40. A method according to claim 34 wherein said testing light includes a plurality of wavelengths absorbable by a plurality of constituents and wherein said circuit means include the means for separately calculating the level of each of said constituents in response to a measured intensity of each of said wavelengths reflected from said tympanic membrane, said method including the steps of directing each of said plurality of wavelengths to said tympanic membrane and measuring an intensity of each wavelength reflected from said tympanic membrane and calculating the level of each of said constituents.

41. A method according to claim 34 wherein said testing light is selected to have at least a wavelength in a range of about 500 to 4000 wave numbers.

42. A method according to claim 41 wherein said testing light is selected to have at least a wavelength of about 1040 wave numbers.

43. An apparatus for determining a level of a constituent in a body fluid, said apparatus comprising:
light generating means for generating a source light including at least one wavelength absorbable by the constituent;
directing means for directing said source light to a tympanic membrane;
light detection means for detecting light reflected from said tympanic membrane and producing an output signal indicative of an amount of absorption of said light by said tympanic membrane; and
processing means for receiving said output signal and calculating an amount of said constituent in a body fluid within said tympanic membrane.

44. An apparatus according to claim 43 wherein said at least one wavelength is in a range of about 500 to about 4000 wave numbers.

45. An apparatus according to claim 44 wherein said at least one wave numbers is about 1040 wavelengths.

46. An apparatus according to claim 43 wherein said light generating means includes means for generating at least two wavelengths including said source light and a reference light of known intensity having at least one wavelength not absorbable by said constituent, said light detection means including means for measuring said source light and said reference light reflected from said tympanic membrane and said processing means including means for comparing said measured intensities and using said measured intensity of said reference light as a reference for determining the amount of said source light absorbed by said constituent.

47. An apparatus according to claim 46 comprising means for multiplexing said source and reference lights emitted from said light generating means.

48. An apparatus according to claim 43 comprising heating means for controlling a temperature of said tympanic membrane.

49. An apparatus according to claim 43 wherein said light generating means and said light detection means are disposed at a distal end of a housing.

50. An apparatus according to claim 49 wherein said housing is sized to be received within an auditory canal of an ear with said distal end opposing said tympanic membrane.

51. An apparatus according to claim 50 wherein said distal end includes a material selected to pass said absorbable wavelength.

52. An apparatus according to claim 51 wherein said absorbable wavelength is infrared.

53. An apparatus according to claim 43 wherein said source light includes a plurality of wavelengths absorbable by a plurality of different constituents and wherein said processing means includes means for separately calculating the level of each of said constituents in response to a measured intensity of each of said wavelengths reflected from said tympanic membrane.

54. An apparatus according to claim 50 wherein said housing includes means for blocking ambient light from entering said auditory canal and reaching said distal end.

55. An apparatus according to claim 43 wherein said fluid is blood.

56. An apparatus according to claim 55 wherein said constituent is glucose.

57. An apparatus according to claim 43 comprising admitting means for admitting a chemical to a body with a level of said constituent in said body fluid changing in response to awn amount of said chemical admitted to said body, control means connecting said processing means to said admitting means for varying an amount of said chemical admitted to said body in response to a level of said constituent calculated by said processing means.

58. An apparatus according to claim 49 comprising heating means for heating said tympanic member to a temperature sufficient for fluid containing vessels in said tympanic membrane to be open.

59. An apparatus according to claim 49 comprising temperature detection means for detecting a temperature of said tympanic membrane.

60. An apparatus according to claim 59 comprising signal means indicating a measured temperature of said tympanic membrane has exceeded a maximum predetermined temperature range.

61. A method for determining a level of a constituent in a body fluid, said method comprising:
generating a source light including at least one wavelength absorbable by the constituent;
directing said source light to a tympanic membrane;
detecting light reflected from said tympanic membrane and producing a signal indicative of an amount of absorption of said light by said tympanic membrane; and
receiving said signal and calculating an amount of said constituent in a body fluid within said tympanic membrane in response to said received signal.

62. A method according to claim 61 wherein said source light is selected to have said at least one wavelength in a range of about 500 to 4000 wave numbers.

63. A method according to claim 62 wherein said at least one wavelength is selected to have a wavelength of about 1040 wave numbers.

64. A method according to claim 61 wherein said method utilizes heating means for heating said tympanic membrane to a temperature sufficient for blood vessels in said tympanic membrane to be unrestricted.

65. A method according to claim 61 wherein further comprising the step of directing a reference light of known intensity having a wavelength non-absorbable by said constituent towards the tympanic membrane and measuring an intensity of said reference light reflected off said tympanic membrane and calculating a level of said constituent by comparing a measured intensity of said reference light to a measured intensity of said source light.

66. A method according to claim 65 comprising multiplexing said reference light and said source light at said light generating means.

67. A method according to claim 65 wherein said constituent is glucose.

68. A method according to claim 65 wherein said wavelength of said source light is infrared.

69. A method according to claim 65 wherein said source light includes a plurality, said method including the steps of directing each of said plurality of wavelengths to said tympanic membrane and measuring an intensity of each wavelength reflected from said tympanic membrane and calculating the level of each of said constituents.

* * * * *

UNITED STATES PATENT AND TRADEMARK OFFICE
CERTIFICATE OF CORRECTION

PATENT NO. : 5,115,133

DATED : May 19, 1992

INVENTOR(S) : Mark B. Knudson

It is certified that error appears in the above-identified patent and that said Letters Patent is hereby corrected as shown below:

Column 3, line 21, "pas" should read --pass--.

Column 5, line 59, insert --(-- after the word "distance".

Column 7, line 24, insert --been-- after the word "have".

Column 12, claim 57, line 4, "awn" should read --an--.

Signed and Sealed this

Thirty-first Day of August, 1993

Attest:

BRUCE LEHMAN

Attesting Officer

Commissioner of Patents and Trademarks